United States Patent [19]

Goel

[11] Patent Number: 4,683,077

[45] Date of Patent: Jul. 28, 1987

[54] REMOVAL OF SMALL AMOUNTS OF WATER FROM MOISTURE CONTAINING CARBOXYLIC ACIDS, ALCOHOLS, OR PHENOLS BY CONTACTING WITH A TETRASUBSTITUTED BICYCLIC AMIDE ACETAL

[75] Inventor: Anil B. Goel, Worthington, Ohio

[73] Assignee: Ashland Oil, Inc., Ashland, Ky.

[21] Appl. No.: 827,578

[22] Filed: Feb. 10, 1986

Related U.S. Application Data

[63] Continuation of Ser. No. 641,238, Aug. 16, 1984, Pat. No. 4,605,746.

[51] Int. Cl.$^4$ ............................................. C09K 3/00
[52] U.S. Cl. .................................. 252/194; 548/217; 548/218
[58] Field of Search ................. 548/217, 218; 252/194

[56] References Cited

U.S. PATENT DOCUMENTS

| | | | |
|---|---|---|---|
| 3,703,468 | 11/1972 | Chess et al. ......................... | 252/194 |
| 4,501,679 | 2/1985 | Reierson et al. ..................... | 548/218 |
| 4,627,932 | 12/1986 | Goel et al. .......................... | 252/194 |

FOREIGN PATENT DOCUMENTS

| | | | |
|---|---|---|---|
| 2344607 | 3/1975 | Fed. Rep. of Germany ...... | 548/218 |
| 2512980 | 12/1975 | Fed. Rep. of Germany ...... | 548/218 |
| 2454740 | 5/1976 | Fed. Rep. of Germany ...... | 548/218 |
| 3143251 | 5/1983 | Fed. Rep. of Germany ...... | 548/218 |
| 3235933 | 3/1984 | Fed. Rep. of Germany ...... | 548/218 |
| 1592467 | 6/1970 | France . | |

OTHER PUBLICATIONS

Seeliger et al., Angen. Chem. Internat. Edit, vol. 5 (1966) No. 10, pp. 875–888.

Primary Examiner—Donald G. Daus
Assistant Examiner—Cecilia Shen
Attorney, Agent, or Firm—John F. Jones

[57] ABSTRACT

Novel bicyclic amide acetals having substituents in the 2, 5 and 7 positions and a process for their preparation are described.

9 Claims, No Drawings

REMOVAL OF SMALL AMOUNTS OF WATER FROM MOISTURE CONTAINING CARBOXYLIC ACIDS, ALCOHOLS, OR PHENOLS BY CONTACTING WITH A TETRASUBSTITUTED BICYCLIC AMIDE ACETAL

This is a continuatin of U.S. patent application Ser. No. 641,238, filed Aug. 16, 1984, now U.S. Pat. No. 4,605,746.

This invention relates to novel substituted bicyclic amide acetals and more particularly pertains to 2, 2, 5, 7 tetra-substituted bicyclic amide acetals and to the process for their preparation.

The bicyclic amide acetals have the general formula I:

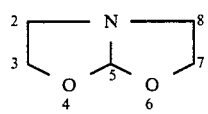

Although unsubstituted, mono-, Di- and tri-substituted bicyclic amide acetals of formula I with substituents at the 3, 5 and 7 positions are known (*Synthesis* 16, 1971), no bicyclic amide acetals with substituents at the 2, 5 and 7 positions were known prior to the time of my invention.

Bicyclic amids acetals, per se, and those with substituents at the 3, 5 and 7 positions are known to react with water, and reactive hydrogen compounds such as alcohols, phenols, carboxylic acids, etc. The bicyclic amide acetals of my invention will react with water but not with phenols, carboxylic acids, etc., which makes them excellent moisture scavengers even in the presence of reactive hydrogen compounds and this property is, indeed, unexpected in view of the prior art.

The novel compositions of my invention are those conforming to the general formula II:

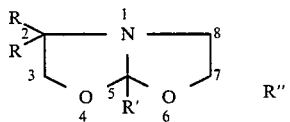

In Formula II, R represents a hydrocarbon group and preferably an alkyl group having from 1 to 10 carbon atoms, R' represents a hydrocarbon group and preferably an alkyl group having from 1 to 20 carbon atoms or an aryl group having from 6 to 10 carbon atoms,, and R" represents a hydrocarbon or ether group, and preferably an alkyl, aralkyl, alkyl ether or aralkyl ether group having from 1 to 20 carbon atoms. The synthesis of the bicyclic amide acetals of my invention involves the reaction of an oxazoline (III) with an epoxide (IV) as shown in the following equation:

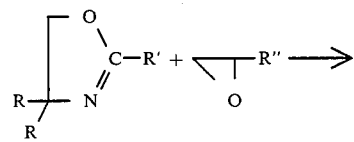

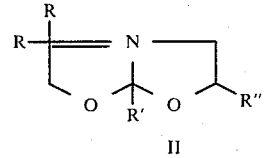

Wherein R, R' and R" have the foregoing designations. The reaction is carried out at a temperature in the range of from 100° to 220° C. and preferably in the range of from 140°–200° C. in a dry inert atmosphere at atmospheric or near atmospheric pressure. The synthesis is advantageously carried out in the presence of a small amount (less than 5% by weight) of catalyst which can be an alkali metal or alkaline earth metal or salt thereof.

The following examples will further illustrate this invention.

EXAMPLE 1

A mixture of 30 g of 2,4,4-trimethyl-2-oxazoline and 39.8 g of 1,2-epoxy-3-phenoxy propane was placed in a glass reactor equipped with a magnetic stirrer, thermometer, condenser and dry nitrogen inlet. To the mixture was added 0.1 g of LiCl and the reaction was carried out at 150°–160° C. with stirring and under a dry nitrogen atmosphere for about 6 hours. GLC analysis showed that more than 95% of the starting oxazoline and epoxide had reacted to give the bicyclic amide acetal (II in which R and R' are methyl and R" is —CH$_2$O Ph). The product was fractionally distilled under reduced pressure (115° C. at 0.1 mm Hg) to give a clear, colorless liquid in about 85% yield.

EXAMPLE 2

The procedure of Example 1 was followed except that 37.8 g of the oxazoline and 38 g of allyl glycidal ether were used. The reaction was carried out at 150° C. for 8½ hours during which time more than 70% of the starting materials reacted to form the bicyclic amide acetal (II in which R and R' are methyl and R" is —CH$_2$O CH=CH$_2$) which was fractionally distilled at 62° C./0.05 mm Hg as a colorless liquid in about 60% yield.

EXAMPLE 3

The procedure of Example 2 was followed using 50.6 g of 2-undecyl-4,4-dimethyl-2-oxazoline and 23 g of the allyl glycidal ether. After 8 hours of reaction at 160° C., GLC analysis indicated that about 85% of the starting materials had reacted. The bicyclic amide acetal product (II in which R is methyl, R' is —C$_{11}$H$_{23}$ and R" is —CH$_2$O—CH$_2$—CH=CH$_2$) was distilled at 125° C./0.1 mm Hg in about 75% yield.

EXAMPLE 4

This Example illustrates the reation of the bicyclic amide acetals of my invention with water. The bicyclic amide acetal prepared in Example 2 (1.24 g) was allowed to react with 0.1 g of water at room temperature (constant temperature bath held at 24° C.) and GLC analysis showed that complete hydrolysis had taken place in about 40 minutes.

EXAMPLE 5

This Example illustrates that the bicyclic amide acetals of this invention do not react with carboxylic acids.

The bicyclic amide acetal of Example 2 (2.249) and hexanoic acid (1.29) were mixed at room temperature under a dry nitrogen atmosphere. The reaction mixture was stirred at room temperature for 2 hours and a portion was silylated with a silylating agent, bis-trimethylsilyl trifluoride acetamide (BSTFA) and analyzed by GLC. The silylating agent is used to inactivate the carboxylic acid to prevent interference in the GLC analysis. This test showed that essentially all of the starting material, both acid and acetal, was still present and that no new material had been formed. The remaining reaction mixture was heated at 60° C. for 5 hours and again analysis of the resulting reaction mixture showed that no reaction had taken place between the carboxylic acid and the substituted bicyclic amide acetal of this invention.

EXAMPLE 6

This experiment which is outside the scope of the present invention demonstrates that substituted bicyclic amide acetals of the prior art do react readily with carboxylic acids. A disubstituted bicyclic amide acetal (II in which R is H, R' is $CH_3CH_2-$ and R" is $-CH_2OCH_2CH=CH_2$) (2.1 g) and 1.2 g of hexanoic acid were allowed to react at 60° C. for 30 minutes and at the end of this time GLC analysis of the reaction mixture showed complete reaction of the starting materials to give the ester-amide-ol product ($HO-CH_2-CH_2-N(-COET)CH_2CH(CH_2OCH_2CH=CH_2)OCOC_5H_{11}$).

EXAMPLE 7

A. This demonstrates that the substituted bicyclic amide acetals of this invention do not react with phenols. A bicyclic amide acetal (of Formula II in which R is $-CH_3$, R' is $-CH_3$ and R" is $-CH_2OCH_2CH=CH_2$) (2.2 g) and 0.95 g of phenol were heated at 130° C. under nitrogen for 2 hours and analyzed by GLC. Only the starting materials were found to be present.

B. A repeat of A of this Example using the prior art bicyclic amide acetal (Formula II in which R is H, R' is Et, and R" is $-CH_2OCH_2CH=CH_2$). In 50 minutes essentially complete reaction of the bicyclic amide acetal and phenol had occurred as determined by GLC analysis.

EXAMPLE 8

This Example illustrates that the tetrasubstituted bicyclic amide acetals of this invention are useful water scavenging agents in the presence of carboxylic acids.

To a mixture of 1.7 g of methacrylic acid and 0.37 g of water was added 4.5 g of tetrasubstituted bicyclic amide acetal (Formula II, R is Me, R' is Me, and R" is $-CH_2OCH_2CH=CH_2$) at room temperature. An exothermic reaction resulted. GLC analysis (after silylation) showed that within two minutes essentially all of the starting tetrasubstituted bicyclic amide acetal had reacted to give the hydrolysis product and that the starting methacrylic acid remained. This indicated that the amide acetals of this invention are selective dehydrating agents and that the hydration reaction is acid catalyzed.

EXAMPLE 9

This demonstrates selective moisture scavenging ability of the tetrasubstituted bicyclic amide acetals of this invention in the presence of phenols.

To a mixture of 2 g of phenol and 0.35 g of water was added 4.6 g of a tetrasubstituted bicyclic amide acetal of Formula II in which R is Me, R' is Me, and R" is $-CH_2OPh$. The reaction mixture was stirred at room temperature for 5 minutes and was then analyzed by GLC which showed the complete conversion of the bicyclic amide acetal to the corresponding hydrolyzed product and that the phenol remained unreacted.

I claim:

1. A process for removing small amounts of water from carboxylic acids, alcohols or phenols comprising contacting a moisture-containing mixture of carboxylic acid or phenol with a tetrasubstituted bicyclic amide acetal conforming to the formula

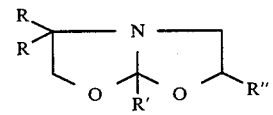

wherein R represents a hydrocarbon group having from 1 to 10 carbon atoms, R' represents a hydrocarbon group having from 1 to 20 carbon atoms, and R" represents a hydrocarbon or ether group having from 1 to 20 carbon atoms and allowing the water and tetrasubstituted bicyclic amide acetal to react.

2. The process of claim 1 wherein R and R' represent alkyl groups and R" represents and alkyl, aralkyl, alkyl ether or aralkyl ether group.

3. The process of claim 2 wherein the bicyclic amide acetal is one in which R and R' are methyl and R" is $-CH_2OC_6H_5$.

4. The process of claim 1 wherein the bicyclic amide acetal is one in which R and R' are methyl and R" is $-CH_2OCH=CH_2$.

5. The process of claim 1 wherein the amide acetal is one in which R is methyl, R' is $-C_{11}H_{23}$ and R" is $-CH_2OCH_2-CH=CH_2$.

6. The process of claim 4 wherein water is removed from a carboxylic acid.

7. The process of claim 6 wherein the carboxylic acid is hexanoic acid.

8. The process of claim 6 wherein the carboxylic acid is methacrylic acid.

9. The process of claim 3 wherein water is removed from phenol.

* * * * *